United States Patent
Uckun et al.

(12) 
(10) Patent No.: US 6,262,053 B1
(45) Date of Patent: Jul. 17, 2001

(54) MELAMINE DERIVATIVES AS POTENT ANTI-CANCER AGENTS

(75) Inventors: Faith M. Uckun, White Bear Lake; Xing-Ping Liu, Minneapolis; Rama Narla, St. Paul, all of MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/338,679

(22) Filed: Jun. 23, 1999

(51) Int. Cl.⁷ .......................... A61K 31/53; A61K 35/00; A61P 35/02; C07D 251/70
(52) U.S. Cl. ............................. 514/245; 544/197
(58) Field of Search .............................. 544/197; 514/245

(56) References Cited

U.S. PATENT DOCUMENTS

| | | | | |
|---|---|---|---|---|
| 4,085,282 | * | 4/1978 | Jones | 544/197 |
| 4,531,979 | * | 7/1985 | Bohler et al. | 148/6.27 |
| 4,617,390 | * | 10/1986 | Hoppe et al. | 544/197 |
| 5,120,844 | * | 6/1992 | Wheeler et al. | 544/209 |
| 5,534,625 | | 7/1996 | Jarman et al. | 544/196 |
| 5,536,722 | | 7/1996 | Coe et al. | 544/198 |
| 5,854,244 | | 12/1998 | Jarman et al. | 544/196 |

FOREIGN PATENT DOCUMENTS

| | | | |
|---|---|---|---|
| 0 517 104 A1 | | 12/1992 | (EP) . |
| 0 796 851 A1 | | 9/1997 | (EP) . |
| 818 450 | * | 1/1998 | (EP) . |
| 06035179 | * | 2/1994 | (JP) . |
| 06095373 | * | 4/1994 | (JP) . |
| WO 93/10116 | | 5/1993 | (WO) . |
| WO 93/20056 | | 10/1993 | (WO) . |
| WO 94/06781 | | 3/1994 | (WO) . |

OTHER PUBLICATIONS

LaBercque et al. Synthesis of Melamines . . . J. Econ. Entomol. 61(6) 1621–32, 1968 CA 70: 27953.*

* cited by examiner

Primary Examiner—Richard L. Raymond
Assistant Examiner—Venkataraman Balasubramanian
(74) Attorney, Agent, or Firm—Merchant & Gould

(57) ABSTRACT

Novel pharmaceutical compositions including melamine derivatives and methods for the treatment of cancer including prostate, brain, breast, and leukemia are described. The methods are directed to administering a therapeutically effective amount of a pharmaceutical composition including melamine derivatives having potent cytotoxic activity.

21 Claims, No Drawings

MELAMINE DERIVATIVES AS POTENT ANTI-CANCER AGENTS

FIELD OF THE INVENTION

This invention relates to melamine derivatives effective for treating tumor cells and particularly effective to induce apoptosis in leukemia and breast tumor cells.

BACKGROUND OF THE INVENTION

Cancer is a major disease that continues as one of the leading causes of death at any age. In the United States alone, it is anticipated that more than a half a million Americans will die of cancer in 1999. Currently, radiotherapy and chemotherapy are two important methods used in the treatment of cancer.

Considerable efforts are underway to develop new chemotherapeutic agents for more potent and specific anti-cancer therapy, presenting effective and efficient cytotoxicity against tumor cells, with minimal interference with normal cell function. Accordingly, there is an urgent need for the development and analysis of novel, effective anti-cancer agents.

SUMMARY OF THE INVENTION

Novel derivatives of melamine have been found to be potent cytotoxic agents with potent activity against cancer cells. For example, certain melamine derivatives were found to exhibit potent cytotoxic activity, particularly against human breast cancer and leukemic cell lines, at micromolar concentrations.

Accordingly, the present invention includes novel compounds and compositions as cytotoxic therapeutic agents, and particularly as anti-tumor agents. The present invention also includes methods for killing tumor cells and/or inhibiting the growth of tumors by administering to a subject an effective antitumor amount of a compound of the invention. Compositions of the invention contain an effective cytotoxic or inhibitory amount of a melamine derivative.

The melamine compounds of the invention have following formula:

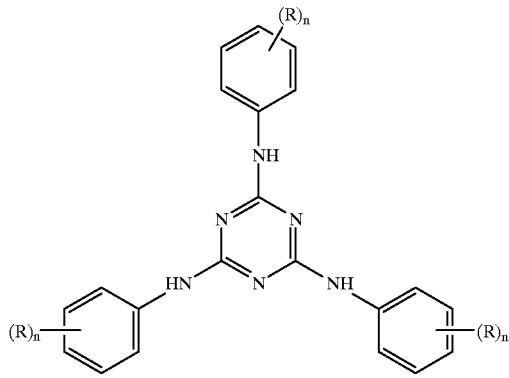

wherein each R is independently selected from the substituents described more fully below, and each n is independently in the range of 1 to 5, preferably 1–3.

Preferred compounds of the invention are those where each R independently comprises one or more halo or hydroxy group, such as those in compounds shown in Table 2 below. Most preferred is 2,4,6-tri(3',5'-dichloro-4'-hydroxy phenyl) amino-1,3,5-triazine (WHI-P239).

DETAILED DESCRIPTION OF THE INVENTION

The present invention includes novel melamine derivatives having potent activity as cytotoxic agents. The compounds of the invention are useful agents in the treatment of cancer for example to inhibit tumor growth or to kill tumor cells, for example, leukemia and breast tumor cells.

Definitions

All scientific and technical terms used in this application have meanings commonly used in the art unless otherwise specified. As used in this application, the following words or phrases have the meanings specified.

As used herein, "alkyl", which includes the alkyl group of "alkoxy" substituents, includes both branched and straight-chain saturated aliphatic hydrocarbon groups having the specified number of carbon atoms. As a preferred embodiment, chains of 1 to 4 carbon atoms are included, for example methyl, ethyl, propyl, isopropyl, butyl, secondary butyl, t-butyl, and the like.

As used herein "halogen" or "halo" substituent includes fluoro, chloro, bromo, and iodo.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to induce apoptosis of leukemia or breast tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

"Treating" or "Treatment" in the context of this invention means the prevention or reduction of severity symptoms or effect of a pathological condition, including prolonging life expectancy. In the context of cancer therapy, treatment includes prevention, of tumor growth, reduction of tumor size, enhanced tumor cell death, and increased apoptosis.

Compounds of the Invention

The novel melamine derivatives of the invention have the general structure represented by the following formula I:

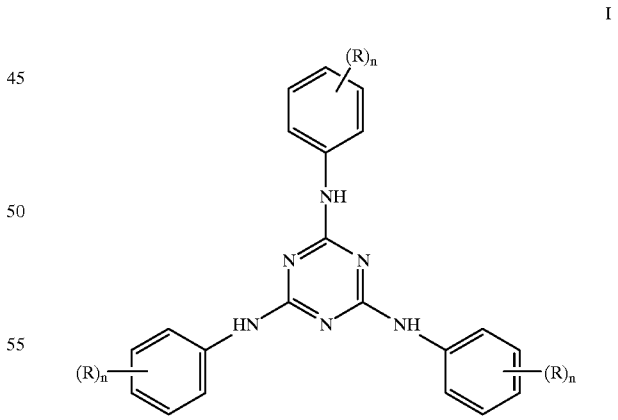

Where each n is independently an integer ranging from 1 to 5 (inclusive), and preferably is 1 to 3.

Each R is independently halo, hydroxy, mercapto, alkyl having 1–4 carbon atoms, alkoxy having 1–4 carbon atoms, thioalkyl of 1–4 carbon atoms, hydroxyalkyl of 1–4 carbon atoms, $NR^1R^2$, nitro, cyano, $CF_3$, COOH, $SO_3H$, $SO_2NR^1R^2$, or $SO_2F$, where $R^1$ and $R^2$ are each independently hydrogen or a $C_1$–$C_4$ alkyl group.

Preferably, each R is independently hydroxy, alkoxy having 1 to 4 carbon atoms, fluoromethyl, or halogen. More preferably, each R is independently hydroxy or halo. Preferred halo is bromo or chloro. A particularly useful compound of the invention is 2,4,6-tri(3'75'-dichloro-4'-hydroxyphenyl)-amino-1,3,5-triazine.

Preferred compounds include those where phenyl groups of formula I are substituted with one or more halogen or hydroxy groups. For example, useful compounds of the invention include those having the following structures:

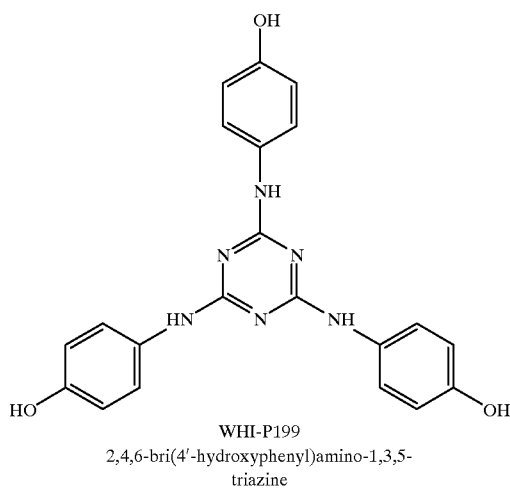

WHI-P199
2,4,6-bri(4'-hydroxyphenyl)amino-1,3,5-triazine

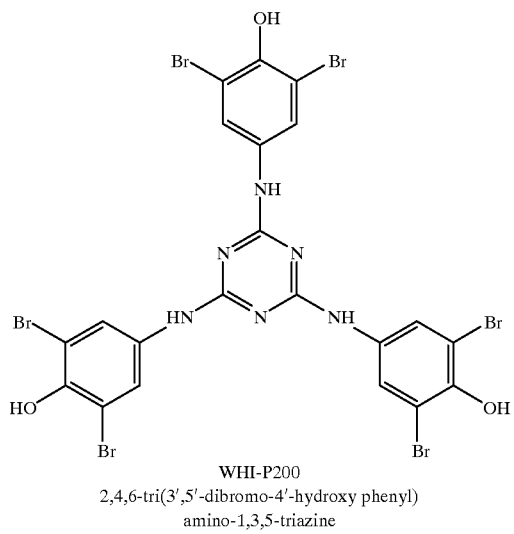

WHI-P200
2,4,6-tri(3',5'-dibromo-4'-hydroxy phenyl)amino-1,3,5-triazine

-continued

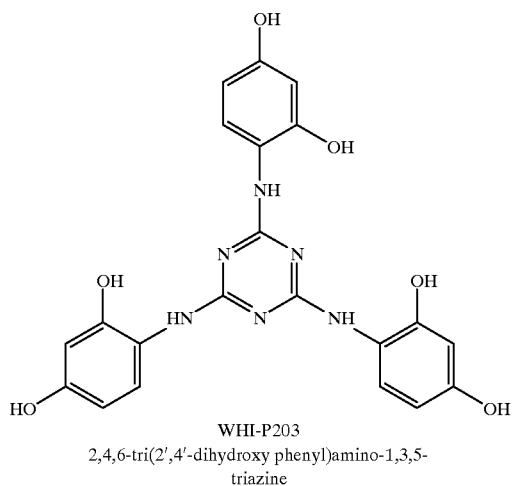

WHI-P203
2,4,6-tri(2',4'-dihydroxy phenyl)amino-1,3,5-triazine

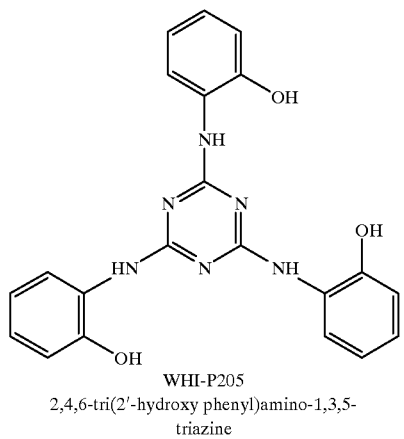

WHI-P205
2,4,6-tri(2'-hydroxy phenyl)amino-1,3,5-triazine

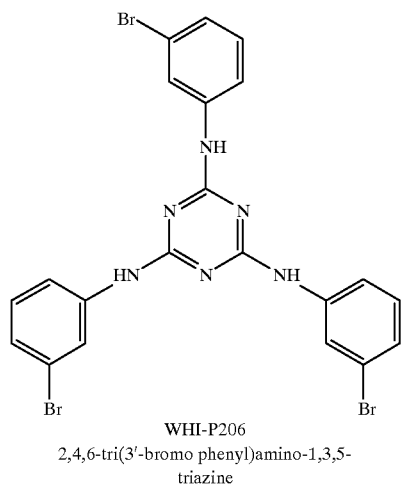

WHI-P206
2,4,6-tri(3'-bromo phenyl)amino-1,3,5-triazine

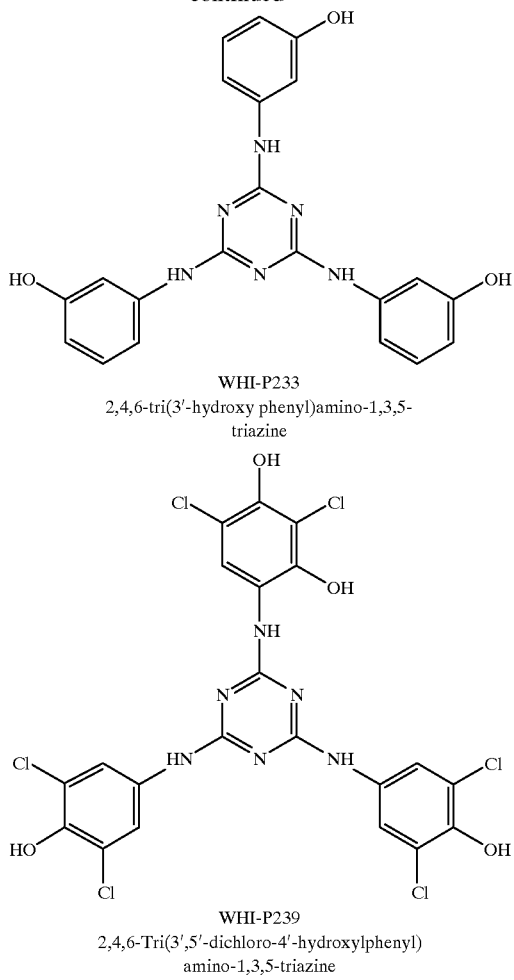

WHI-P233
2,4,6-tri(3'-hydroxy phenyl)amino-1,3,5-triazine

WHI-P239
2,4,6-Tri(3',5'-dichloro-4'-hydroxylphenyl)amino-1,3,5-triazine

Although the triazine compounds of invention has been exemplified above where each of the three substituted phenyl groups

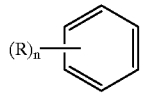

are identical, it is understood that each substituted phenyl group can be the same or different. Synthesis of compounds where the substituted phenyl groups are identical is more easily accomplished, however synthetic schemes for the production of compounds having different substituted phenyl groups are known.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Examples of suitable amines are N,N'-dibenzylethylenediamine, chloroprocaine, choline, diethanolamine, ethylenediamene, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the invention.

Melamine compounds of the present invention, such as the exemplary melamine derivative, 2,4,6-tri(3',5'-dichloro-4'-hydroxyphenyl)-amino-1,3,5-triazine (WHI-P239), can be prepared by the condensation of cyanuric chloride with 3,5-dichloro-4-hydroxyaniline as shown in Scheme 1. This synthesis scheme serves to illustrate the general scheme that can be used for the synthesis of other melamine derivatives of the invention. Reactants for the synthesis of WHI-P239 and other melamine derivatives of the invention are commercially available and/or prepared by known methods.

Synthesis procedure of Melamine derivatives

To a solution of cyanuric chloride in THF is added the desired substituted aniline (1:3 molar ratio) with stirring for about 2–4 hours at room temperature. The reaction mixture is then refluxed 1–2 days and an excess amount of $Et_3N$ is added. All solvent is evaporated and the crude is recrystalized from DMF to yield the desired melamine product. The synthetic procedure is diagramed below in Scheme 1.

Scheme 1

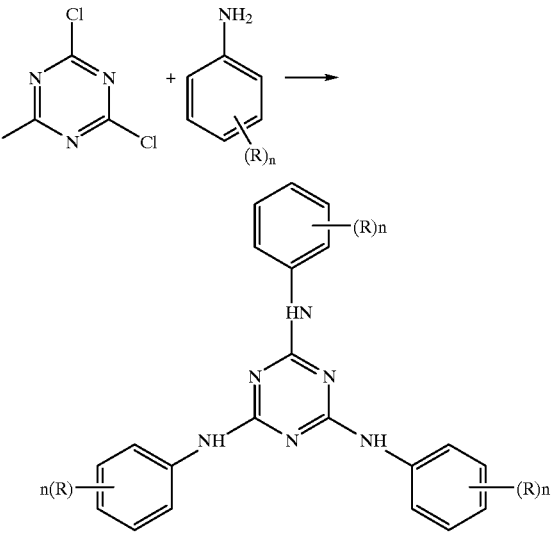

To prepare compounds of the invention where the three substituted phenyl groups are not identical, a mixture of anilines can be used in the reaction mixture. Alternatively, additional sites (e.g., Cl) can be blocked for selective addition of one substituted phenyl group at a time. Further, selective modification of the substituted phenyl groups may be performed after synthesis of the melamine derivitive by known methods.

Cytotoxic Compounds

The compounds of the invention are effective cytotoxic agents, for example, against tumor cells such as leukemic and breast cancer cells. In the methods of the invention, the cytotoxic effects of melamine derivatives are achieved by contacting cells, such as tumor cells, with micromolar amounts of the inhibitory compound. By way of example, a particularly useful anti-tumor agent is 2,4,6-tri-(3',5'-dichloro-4'-hydroxyphenyl)-amino-1,3,5-triazine (P-239) as shown in the Examples below.

Tumor Treatment

The compounds of the invention can be used in methods of tumor treatment, for example, by administering to a subject a compound of the invention in order to achieve an inhibition of tumor cell growth, a killing of tumor cells, induced apoptosis, and/or increased patient survival time.

The cytotoxic compounds of the invention are suitable for use in mammals. As used herein, "mammals" means any class of higher vertebrates that nourish their young with milk secreted by mammary glands, including, for example, humans, rabbits, and monkeys.

Administration Methods

The compounds of the present invention can be formulated as pharmaceutical compositions and administered to a mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

The compounds can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleageneous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes.

More preferably, the compounds of the present invention are administered parenterally, i.e., intravenously or intraperitoneally, by infusion or injection. In one embodiment of the invention, the compounds may be administered directly to a tumor by tumor injection; or by systemic delivery by intravenous injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on the tumor cells to be treated. For example, antigens present on B-lineage cancer cells, such as CD19, can be targeted with anti-CD19 antibodies such as B43. Antibody fragments, including single chain fragments, can also be used. IL4 can also be used to target B-cells. Cancer cells expressing EGF or IGF receptors can be targeted with the binding ligand. Other such ligand-receptor binding pairs are known in the scientific literature for specific cancers. Methods for producing conjugates of the compounds of the invention and the targeting moieties are known.

Useful Dose

When used in vivo to kill tumor cells, the administered dose is that effective to have the desired effect, such as sufficient to reduce or eliminate tumors. Appropriate amounts can be determined by those skilled in the art, extrapolating using known methods and relationships, from the in vitro data provided in the Examples.

In general, the dose of the novel melamine derivatives compounds effective to achieve tumor cell apoptosis, reduction in tumors, and increased survival time, is 1–100 mg/kg body weight/dose for a direct targeted administration.

The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100 mg/kg body weight is expected to be effective, although more or less may be useful.

In addition, the compositions of the invention may be administered in combination with other anti-tumor therapies. In such combination therapy, the administered dose of the melamine derivatives may be less than for single drug therapy.

EXAMPLES

The invention may be further clarified by reference to the following Examples, which serve to exemplify some of the embodiments, and not to limit the invention in any way.

Example 1

Synthesis and Characterization of 2,4,6-tri(3',5'-dichloro-4'-hydroxyphenyl)-amino-1,3,5-triazine (WHI-P239)

All chemicals were purchased from the Aldrich Chemical Company, Milwaukee, Wis., and were used directly for synthesis. Anhydrous solvents such as acetonitrile, methanol, ethanol, ethyl acetate, tetrahydrofuran, chloroform, and methylene chloride were obtained from Aldrich as sure seal bottles under nitrogen and were transferred to reaction vessels by cannulation. All reactions were carried out under a nitrogen atmosphere.

The compound 2,4,6-tri(3',5'-dichloro-4'-hydroxylphenyl)-amino-1,3,5-triazine(WHI-P239) was prepared through the condensation of cyanuric chloride with 3,5-dichloro-4-hydroxylaniline as shown in Scheme 1.

Scheme 1

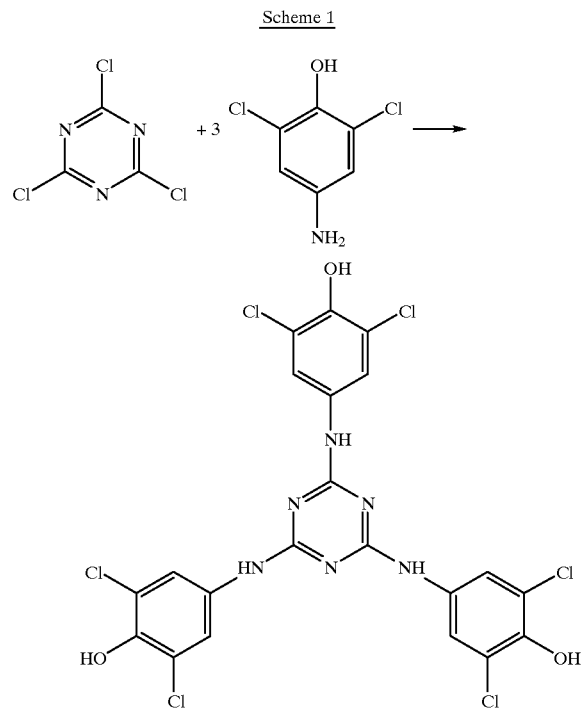

Specifically for the synthesis of WHI-P239, the following method was used. To a solution of 920 mg (5 mmol) of cyanuric chloride in 500 ml of THF was added 2.62 g (15 mmol) of 4-amino-2,6-dichlorophenol with stirring for 2 hours at room temperature. The reaction mixture was then refluxed 15 hours and an excess amount of $Et_3N$ was added. All solvent was evaporated and the crude was recrystalized from DMF to yield 2.4 g of product.

Yield 82.53%. m.p.>300.0° C.

The following melamine compounds were synthesized as described above and characterized. Each structure is shown below in Table 1. The identifying analytical test results for each compound are also shown below. Proton and carbon Nuclear Magnetic Resonance ($^1$H and $^{13}$C NMR) spectra were recorded on a Mercury 2000 Varian spectrometer operating at 300 MHz and 75 MHz, respectively, using an automatic broad band probe. Unless otherwise noted, all NMR spectra were recorded in $CDCl_3$ at room temperature. $^1$H chemical shifts are quoted in parts per million (δ in ppm) downfield from tetramethyl silane (TMS), which was used as an internal standard at 0 ppm and s, d, t, q, m designate singlet, doublet, triplet, quartet and multiplet, respectively. Melting points were determined using a Fisher-Johns melting apparatus and are uncorrected. UV spectra were recorded using a Beckmann Model # DU 7400 UVNV is spectrometer with a cell path length of 1 cm. Methanol was used as the solvent for the UV spectra. Fourier Transform Infrared spectra were recorded using an FT-Nicolet model Protege #460 instrument. The infrared spectra of the liquid samples were run as neat liquids using KBr discs. The KBr pellet method was used for all solid samples. The GC/mass spectrum analysis was conducted using a Hewlett-Packard GC/mass spectrometer model # 6890 equipped with a mass ion detector and Chem Station software. The temperature of the oven was steadily increased from 70° C. to 250° C. and the carrier gas was helium.

2,4,6-Tri(4'-hydroxylphenyl)-amino-1,3,5-triazine(WHI-P199).

Yield 82.53%, m.p. 280.0–282.0° C. $^1$H NMR(DMSO-d$_6$): d 10.16(s, brod, 3H, —NH), 9.47(s, 3H, —OH), 7.35(s, 6H, 2',6'—H), 6.76(s, 6H, 3',5' —H). UV(MeOH): 206.0, 276.0, 349.0 nm. IR(KBr)u$_{max}$: 3372, 3257, 2935, 1626, 1512, 1380, 1225 cm$^{-1}$. GC/MS m/z 403(M$^+$+1, 25.45), 402(M$^+$,100.00), 401(M$^+$-1, 22.20),311(22.20), 310(12.91), 309(17.59.), 135(15.56), 134(19.26).

2,4,6-Tri(3',5'-dibromo-4'-hydroxylphenyl)-amino-1,3,5-triazine(WHI-P200).

Yield 91.63%, m.p. 248.0–250.0° C. $^1$H NMR(DMSO-d$_6$): d 9.36(s, 3H, —NH), 7.84(s, 6H, 2', 6'—H). UV(MeOH): 203.0, 214.0 , 280.0 nm. IR(KBr)u$_{max}$: 3473, 3381, 3070, 2993, 1624, 1500, 1471, 1161 cm$^{-1}$. GC/MS m/z 882(M$^+$+6, 7.51), 881 (M$^+$+5,30.36), 880(M$^+$+4,18.95), 879(M$^+$+3, 74.63), 878(M$^+$+2, 25.72), 877(M$^+$+1, 100.00), 876(M$^+$,100.00), 875(M$^+$-1,76.04), 795(29.20), 614 (18.00), 613 (41.50).

2,4,6-Tri(2',4'-Dihydroxylphenyl)-amino-1,3,5-triazine (WHI-P203)

Yield 88.61%, m.p.205.0° C.(dec.). $^1$H NMR(DMSO-d$_6$): d 10.60(s, 3H, —NH), 9.70(s, 6H, —OH), 7.12(d, J$_{5', 6'}$=8.7 Hz, 3H, 6'—H), 6.55(d, J$_{5', 3'}$=2.7 Hz, 3H, 3' —H), 7.12(dd, J$_{5', 6'}$=8.7 Hz, J$_{5', 3'}$=2.7 Hz, 3H, 5'—H). $^{13}$C NMR(DMSO-d$_6$): d 158.12, 151.7, 124.60, 110.06, 106.30, 103.22. UV(MeOH):. 207.0, 265.0, 296.0 nm. IR u$_{max}$ (KBr): 3211, 2868, 1626, 1510, 1457, 1346, 1038 cm$^{-1}$.

2,4,6-Tri(2'-hydroxylphenyl)-amino-1,3,5-triazine(WHI-P205)

Yield 98.00%; m.p. 225.0–227.0° C. $^1$H NMR(DMSO-d$_6$): d 10.02(s, broad, 3H, -NH), 9.47(s, 3H, —OH), 7.58–6.82(m, 12H, Ph-H). UV(MeOH):. 207.0, 265.0, 296.0 nm. IR(KBr)u$_{max}$: 3211, 2868, 1626, 1510,1457, 1346, 1038 cm$^{-1}$.

2,4,6-Tri(3'-bromophenyl)-amino-1,3,5-triazine(WHI-P206).

Yield 82.53%, m.p.193.0–196.0 C. $^1$H NMR(DMSO-d$_6$): d 9.31(s, brod, 3H, —NH), 7.75–6.99(m, 12H, 2',4',5',6' —H). UV(MeOH): 217.0, 276.0, 328.0 nm. IR(KBr)u$_{max}$: 3398, 3272, 2929, 1630, 1567, 1478, 1220, 1066 cm$^{-1}$. GC/MS m/z 592(M$^+$+1,99.47), 591(M$^+$, 55.06), 590(M$^+$-1, 100,00), 511(5.21), 431(3.49), 378(19.79).

2,4,6-Tri(3'-hydroxyphenyl)-amino-1,3,5-triazine(WHI-P233).

Yield 98.00%, m.p.270.0–271.0° C. $^1$H NMR(DMSO-d$_6$): d 11.28(s, 3H, —NH), 9.91(s, 3H, —OH), 7.27–6.52 (m, 12H, 2',4',5',6'—H). UV(MeOH):. 219.0, 272.0, 288.0 nm. IR(KBr)u$_{max}$: 3325, 3113, 2877, 1608, 1456, 1363, 1159 cm$^{-1}$. Found: C, 57.44; H, 4.41; N, 19.12. C$_{21}$H$_{18}$N$_6$O$_3$.HCl requires: C, 57.44; H, 4.41; N, 19.12%.

2,4,6-Tri(3',5'-dichloro-4'-hydroxylphenyl)-amino-1,3,5-triazine(WHI-P239).

Yield 79.21%; m.p.>300.0° C. $^1$H NMR(DMSO-d$_6$): d 9.44(s, 3H, —HN), 7.69(s, 6H, Ph-H). UV(MeOH): 211.0, 249.0, 339.0 nm. IR(KBr)u$_{max}$: 3241, 2839, 2783, 1635, 1580, 1514, 1420, 1360, 1281 cm$^{-1}$.

The following melamine derivatives described in Table 1 were prepared according to the above method.

TABLE 1

| | | Melamine Derivatives of the Invention | | |
|---|---|---|---|---|
| No | Name | Structure | Formula | MW |
| 1 | P-199 | | C$_{21}$H$_{18}$N$_6$O$_3$ | 402 |

TABLE 1-continued

Melamine Derivatives of the Invention

| No | Name | Structure | Formula | MW |
|---|---|---|---|---|
| 2 | P-200 | 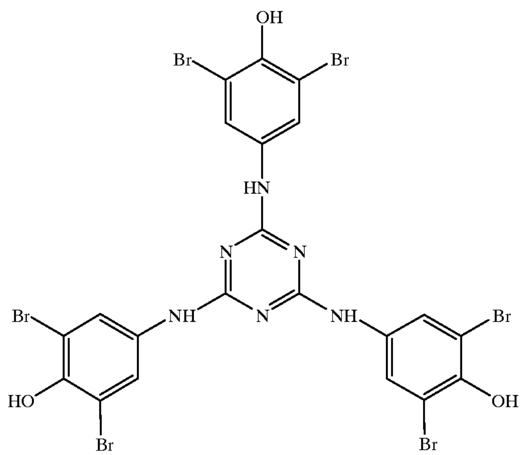 | $C_{21}H_{12}Br_6N_6O_3$ | 877 |
| 3 | P-203 | 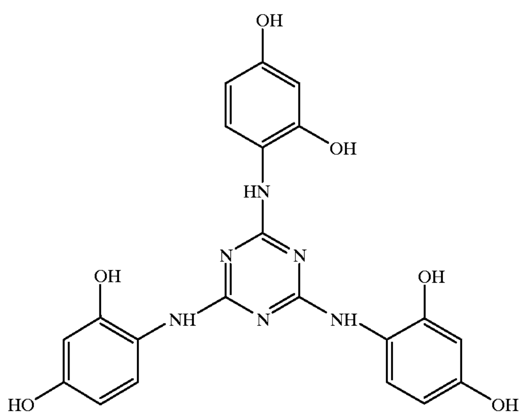 | $C_{21}H_{18}N_6O_6$ | 450 |
| 4 | P-205 | 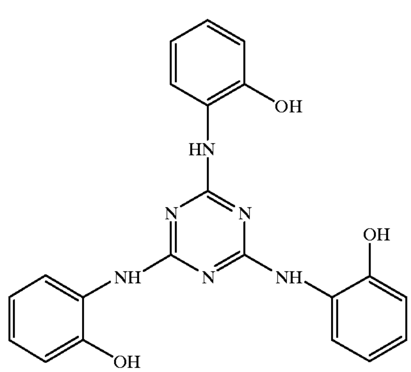 | $C_{21}H_{18}N_6O_3$ | 402 |

TABLE 1-continued

Melamine Derivatives of the Invention

| No | Name | Structure | Formula | MW |
|----|------|-----------|---------|-----|
| 5 | P-206 | 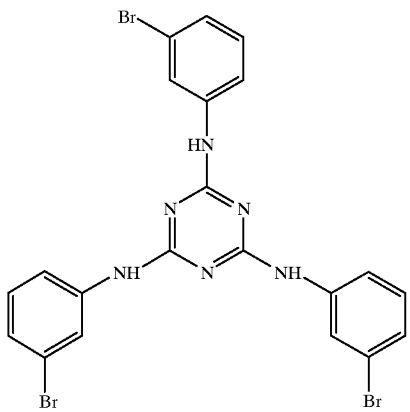 | $C_{18}H_{15}Br_3N_6$ | 591 |
| 6 | P-233 | 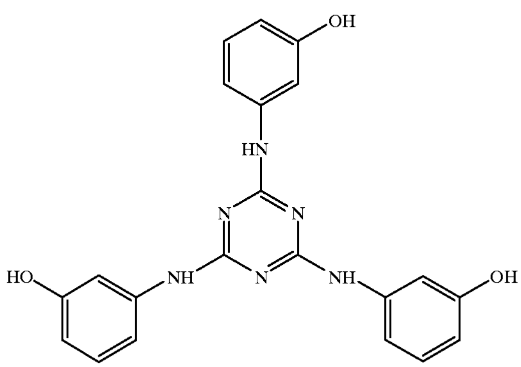 | $C_{21}H_{18}N_6O_3$ | 402 |
| 7 | P-239 | 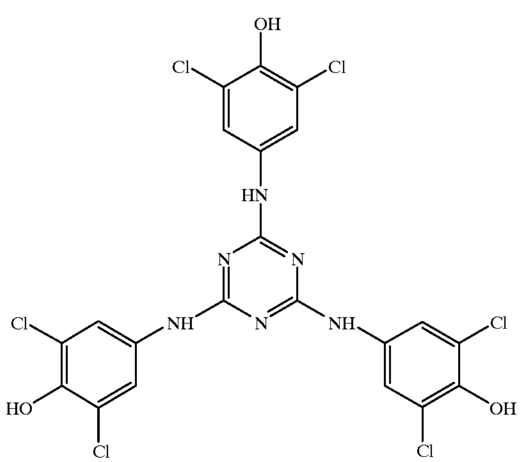 | $C_{21}H_{12}Cl_6N_6O_3$ | 606 |

Example 2

Cytotoxicity of Melamine Derivatives

The cytotoxicity of melamine derivatives against tumor cells was evaluated in leukemic cells and breast cancer cells.

Cytotoxicity Assay

Cytotoxicity of various compounds against tumor cells was performed using the MTT (3-[4,5-dimethylthiazol-2-yl]-2,5-diphenyl tetrazolium bromide) assay (Boehringer Mannheim Corp., Indianapolis, Ind.). Unless otherwise specified, all cell lines were obtained from the American Type Culture Collection (ATCC). Briefly, exponentially growing cells were seeded into a 96-well plate at a density of $2.5 \times 10^4$ cells/well and incubated for 36 hours at 37° C. prior to drug exposure. On the day of treatment, culture medium was carefully aspirated from the wells and replaced with fresh medium containing WHI-P239 at concentrations ranging from 0.1 to 250 μM. Triplicate wells were used for each treatment.

Human leukemic cell lines (NALM-6, MOLT-3), human breast tumor cells (BT20), prostate cancer cells (PC3), and glioblastoma cells (U373) were obtained from the American Type Culture Collection and maintained as a continuous cell line in Dulbecco's modified Eagles's medium supplemented with 10% fetal bovine serum and antibiotics.

The cells were incubated with the various compounds for 24–36 hours at 37° C. in a humidified 5% $CO_2$ atmosphere. To each well, 10 μl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbence of each well was measured in a microplate reader (Labsystems) at 540 nm and a reference wavelength of 690 in. To translate the $OD_{540}$ values into the number of live cells in each well, the $OD_{540}$ values were compared to those on standard $OD_{540}$-versus-cell number curves generated for each cell line. The percent survival was calculated using the formula shown below. The $IC_{50}$ values were calculated by non-linear regression analysis and are shown in Table 2.

$$\% \text{ Survival} = \frac{\text{live cell number [test]}}{\text{live cell number [control]}} \times 100$$

TABLE 2

Cytotoxicity in Tumor Cells $IC_{50}$ (μM)

| Compound | NALM-6 Leukemia | BT-20 Breast Cancer | PC-3 Prostate Cancer | U373 Brain Tumor |
|---|---|---|---|---|
| WHI-P199 | >250 | 240.2 | 221.3 | >250 |
| WHI-P233 | 5.1 | 66.1 | 45.1 | 104.4 |
| WHI-P205 | 21.5 | 107.6 | 102.1 | 224.3 |
| WHI-P200 | 10.1 | 27.1 | 64.5 | >250 |
| WHI-P239 | 9.8 | 13.2 | 31.5 | 155.1 |
| WHI-P206 | >250 | >250 | >250 | >250 |

The most effective compound against leukemia cells was WHI-P233. The ranking order of the antileukemic potency was: WHI-P233 ($IC_{50}$=5.1 EM)>WHI-P239 ($IC_{50}$=9.8 μM)>WHI-P200 ($IC_{50}$=10.1 μM)>WHI-P205 ($IC_{50}$=21.5 μM). Compounds WHI-P199 and WHI-P206 had no antileukemic activity ($IC_{50}$>250 μM).

The most effective compound against breast cancer cells was WHI-P239. The ranking order of the anti-breast cancer potency was: WHI-P239 ($IC_{50}$=13.2 μM)>WHI-P200 ($IC_{50}$=27.1 μM)>WHI-P233 ($IC_{50}$=66.1 μM)>WHI-P205 ($IC_{50}$=107.6 μM)>WHI-P 199 ($IC_{50}$=240.2 μM). Compound WHI-p206 exhibited no cytotoxic activity against breast cancer cells ($IC_{50}$>250 μM).

The most effective compound against prostate cancer cells was WHI-P239. The ranking order of anti-prostate cancer activity was: WHI-P239 ($IC_{50}$=31.5 μM)>WHI-P233 ($IC_{50}$=45.1 μM)>WHI-P200 ($IC_{50}$=64.5 μM)>WHI-P205 ($IC_{50}$=102.1 μM)>WHI-P199 ($IC_{50}$=221.3 μM)>WHI-P206 ($IC_{50}$>250 μM). These compounds were least active against brain tumor cells.

The ranking order of anti-glioblastoma activity was: WHI-P233 ($IC_{50}$=104.4 μM)>WHI-P239 ($IC_{50}$=155.1 μM)>WHI-P205 ($IC_{50}$=224.3 μM). Compounds WHI-P200 and WHI-P206 exhibited no cytotoxic activity against brain tumor cells.

All publications, patents, and patent documents described herein are incorporated by reference as if fully set forth. The invention described herein may be modified to include alternative embodiments. All such obvious alternatives are within the spirit and scope of the invention, as claimed below.

We claim:

1. A pharmaceutical composition comprising a therapeutically effective amount of a compound of the formula

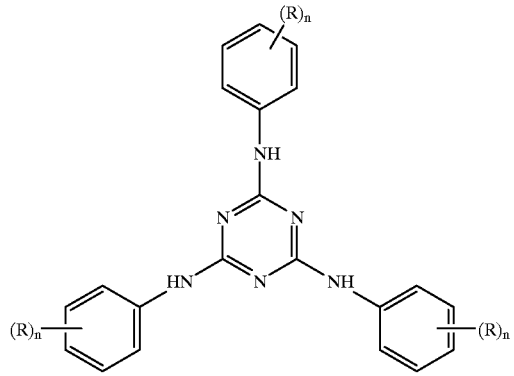

wherein each n is independently an integer of 1 to 5; and each R of the compound is independently hydroxy, ($C_1$–$C_4$) alkoxy, trifluoromethyl, or selected from the group consisting of 2', 3', 4', 5', or 6' bromo, 2', 3', 4', 5', or 6' fluoro, 2', 3', 4', 5', or 6' iodo, and 4' chloro; or a pharmaceutically acceptable acid addition salt thereof, and a pharmaceutically acceptable carrier or diluent.

2. The pharmaceutical composition of claim 1, wherein each R of the compound is independently, hydroxy or selected from the group consisting of 2', 3', 4', 5', or 6' bromo, 2', 3', 4', 5', or 6' fluoro, 2', 3', 4', 5', or 6' iodo, and 4' chloro.

3. The pharmaceutical composition of claim 1, wherein each R of the compound is independently hydroxy, ($C_1$–$C_4$) alkoxy, trifluoromethyl, or selected from the group consisting of 2', 3', 4', 5', or 6' bromo, and 4' chloro .

4. A pharmaceutical composition comprising a therapeutically effective amount of a compound of the formula

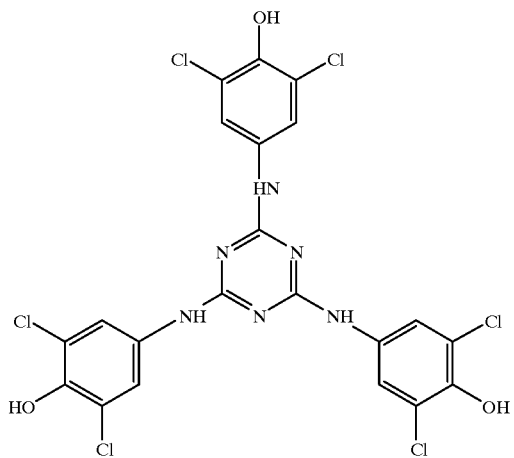

or a pharmaceutically acceptable acid addition salt thereof; and a pharmaceutically acceptable carrier or diluent.

5. The pharmaceutical composition of claim 1, wherein at least one R of the compound is selected from the group consisting of 2', 3', 4', 5', or 6' bromo, 2', 3', 4', 5', or 6' fluoro, 2', 3', 4', 5', or 6' iodo, and 4' chloro.

6. A pharmaceutical composition comprising a therapeutically effective amount of a compound of the formula

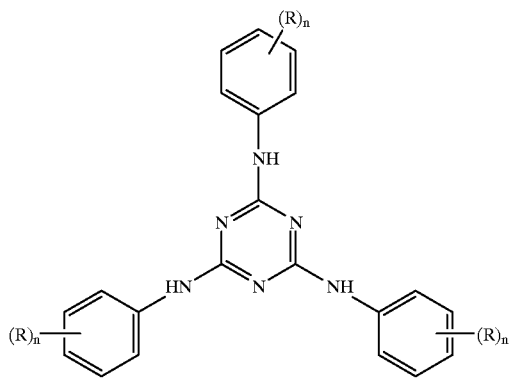

wherein each n is independently an integer of 1 to 5; and
each R is independently hydroxy, $(C_1-C_4)$ alkoxy, trifluoromethyl, or halo, wherein at least one R of the compound is hydroxy; or a pharmaceutically acceptable acid addition salt thereof; and a pharmaceutically acceptable carrier or diluent.

7. A pharmaceutical composition, comprising a therapeutically effective amount of a compound of the formula

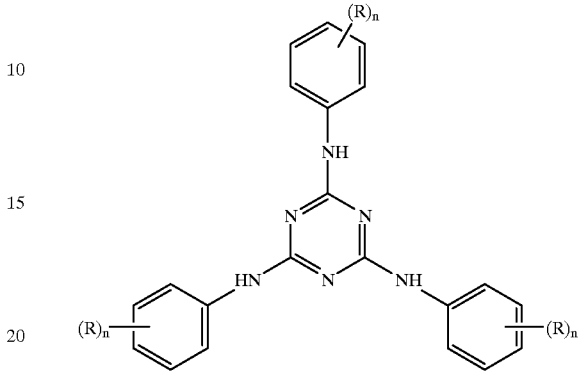

wherein each n is independently an integer of 1 to 5; and each R of the compound is independently hydroxy, $(C_1-C_4)$ alkoxy, trifluoromethyl, or halo;

wherein at least one R of the compound is bromo; or a pharmaceutically acceptable acid addition salt thereof; and a pharmaceutically acceptable carrier or diluent.

8. A pharmaceutical composition, comprising a therapeutically effective amount of a compound of the formula

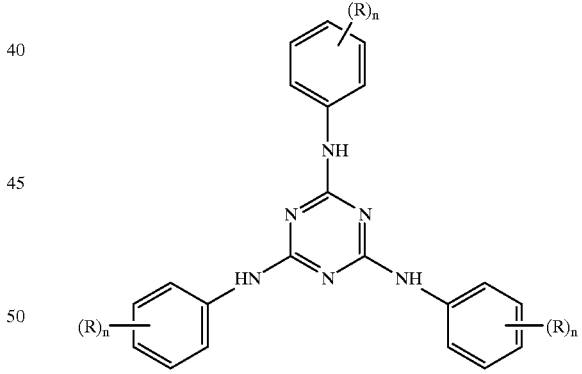

wherein each n is independently an integer of 1 to 5; and each R of the compound is independently hydroxy, $(C_1-C_4)$ alkoxy, trifluoromethyl, or halo;

wherein at least one R of the compound is 4'-hydroxy; or a pharmaceutically acceptable acid addition salt thereof; and a pharmaceutically acceptable carrier or diluent.

9. A pharmaceutical composition, comprising a therapeutically effective amount of a compound of the formula

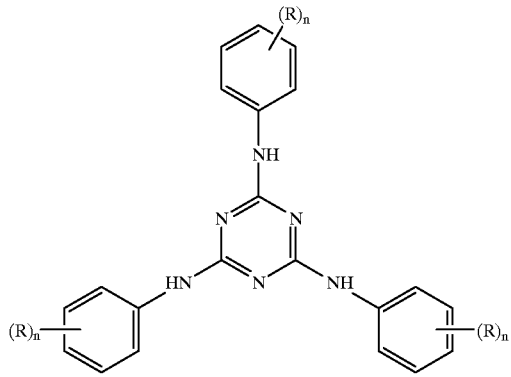

wherein each n is independently an integer of 1 to 5; and each R of the compound is independently hydroxy, $(C_1-C_4)$ alkoxy, trifluoromethyl, or halo;

wherein at least two R groups of the compound are 2'-hydroxy and 4'-hydroxy; or a pharmaceutically acceptable acid addition salt thereof; and a pharmaceutically acceptable carrier or diluent.

10. A pharmaceutical composition, comprising a therapeutically effective amount of a compound of the formula

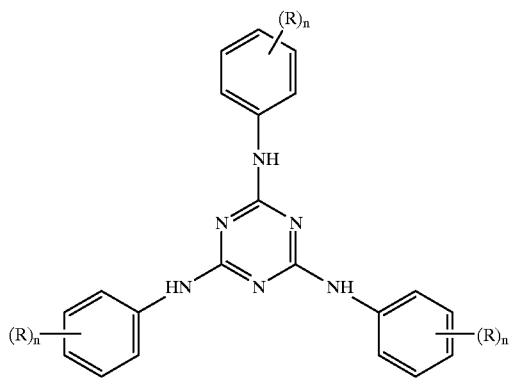

wherein each n is independently an integer of 1 to 5; and each R of the compound is independently hydroxy, $(C_1-C_4)$ alkoxy, trifluoromethyl, or halo;

wherein at least one R of the compound is 3'-bromo; or a pharmaceutically acceptable acid addition salt thereof, and a pharmaceutically acceptable carrier or diluent.

11. A pharmaceutical composition, comprising a therapeutically effective amount of a compound of the formula

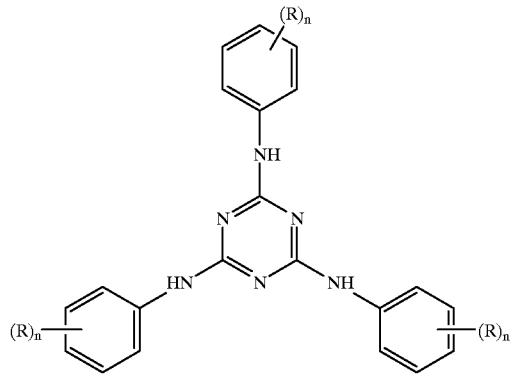

wherein each n is independently an integer of 1 to 5; and each R of the compound is independently hydroxy, $(C_1-C_4)$ alkoxy, trifluoromethyl, or halo;

wherein at least 3 R groups of the compound are 3'-bromo, 5'-bromo and 4'-hydroxy; or a pharmaceutically acceptable acid addition salt thereof; and a pharmaceutically acceptable carrier or diluent.

12. A pharmaceutical composition, comprising a therapeutically effective amount of a compound of the formula

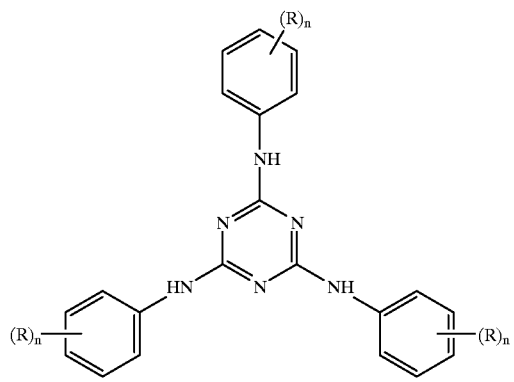

wherein each n is independently an integer of 1 to 5; and each R of the compound is independently hydroxy, $(C_1-C_4)$ alkoxy, trifluoromethyl, or halo;

wherein at least one R of the compound is 2'-hydroxy; or a pharmaceutically acceptable acid addition salt thereof; and a pharmaceutically acceptable carrier or diluent.

13. A pharmaceutical composition, comprising a therapeutically effective amount of a compound of the formula

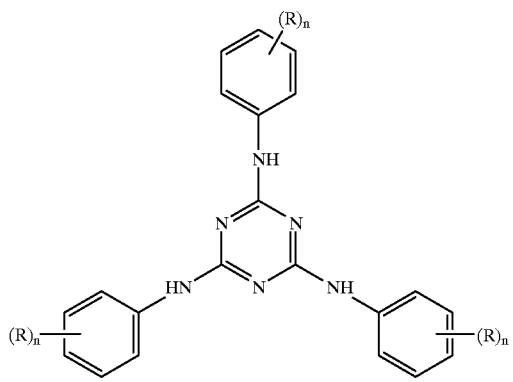

wherein each n is independently an integer of 1 to 5; and each R of the compound is independently hydroxy, $(C_1-C_4)$ alkoxy, trifluoromethyl, or halo;

wherein at least one R of the compound is 3'-hydroxy; or a pharmaceutically acceptable acid addition salt thereof, and a pharmaceutically acceptable carrier or diluent.

14. A method for inhibiting growth of tumor cells in a subject comprising administering to said subject an effective inhibiting amount of a compound of the formula

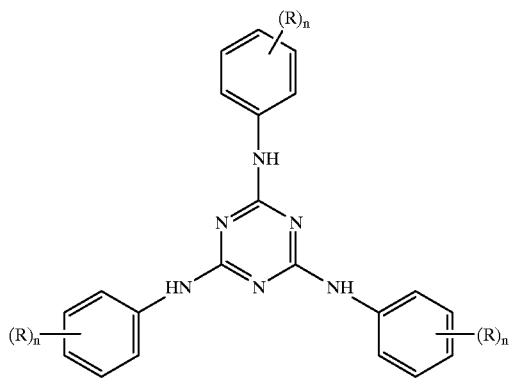

wherein each n is independently an integer of 1 to 5;

each R is independently halogen, hydroxy, mercapto, acyl, mercaptoalkyl, $(C_1-C_4)$ alkyl, $(C_1-C_4)$ alkoxy, (CI-$C_4$) alkylthio, (CI-$C_4$) hydroxyalkyl, $NR^1R^2$, nitro, cyano, $CF_3$, COOH, $SO_3H$, $SO_2NR^1R^2$ or $SO_2F$, where $R^1$ and $R^2$ are each independently hydrogen or $(C_1-C_4)$ alkyl; or a pharmaceutically acceptable acid addition salt thereof.

15. The method of claim 14, wherein said inhibiting comprises inducing apoptosis of said tumor cell.

16. A method of treating prostate cancer or brain cancer in a subject comprising administering a therapeutically effective amount of a compound of the formula

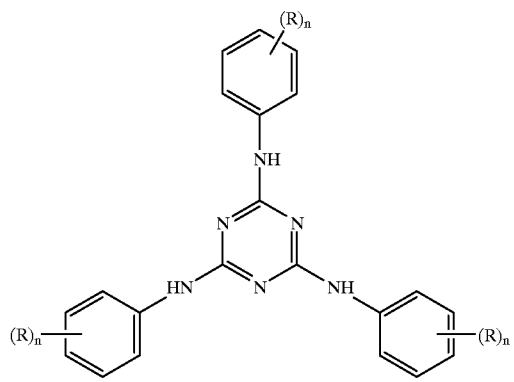

wherein each n is independently an integer of 1 to 5;

each R is independently halogen, hydroxy, mercapto, acyl, mercaptoalkyl, $(C_1-C_4)$ alkyl, $(C_1-C_4)$ alkoxy, $(C_1-C_4)$ alkylthio, $(C_1-C_4)$ hydroxyalkyl, $NR^1R^2$, nitro, cyano, $CF_3$, COOH, $SO_3H$, $SO_2NR^1R^2$ or $SO_2F$, where $R^1$ and $R^2$ are each independently hydrogen or $(C_1-C_4)$ alkyl, or a pharmaceutically acceptable acid addition salt thereof.

17. A method for inducing cytotoxicity in a tumor cell comprising:

administering to said tumor cell a cytotoxic dose of a compound of the formula

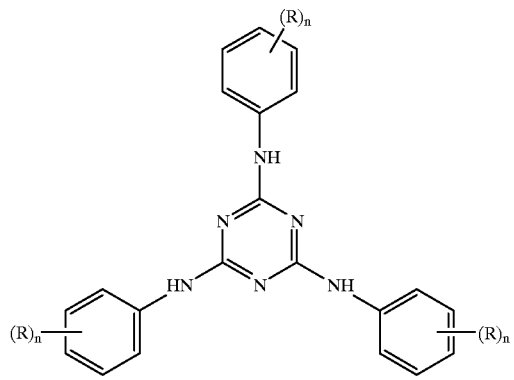

wherein each n is independently an integer of 1 to 5;

each R is independently halogen, hydroxy, mercapto, acyl, mercaptoalkyl, $(C_1-C_4)$ alkyl, $(C_1-C_4)$ alkoxy, $(C_1-C_4)$ alkylthio, $(C_1-C_4)$ hydroxyalkyl, $NR^1R^2$, nitro, cyano, $CF_3$, COOH, $SO_3H$, $SO_2NR^1R^2$ or $SO_2F$, where $R^1$ and $R^2$ are each independently hydrogen or (C I-$C_4$) alkyl; or a pharmaceutically acceptable acid addition salt thereof.

18. The method of claim 17, wherein said compound is 2,4,6-tris(4'-hydroxyphenyl amino)-1,3,5-triazine;

2,4,6-tris(3',5'-dibromo-4'-hydroxy phenyl amino)-1,3,5-triazine;

2,4,6-tris(2',4'-dihydroxy phenyl amino)-1,3,5-triazine;

2,4,6-tris(2'-hydroxy phenyl amino)-1,3,5-triazine;

2,4,6-tris(3'-bromo phenyl amino)-1,3,5-triazine;

2,4,6-tris(3'-hydroxy phenyl amino)-1,3,5-triazine; or 2,4,6-tris(3',5'-dichloro-4'-hydroxylphenyl amino)-1,3,5-triazine.

19. The method of claim 18, wherein said compound is 2,4,6-tris(3',5'-dichloro-4'-hydroxylphenyl amino)-1,3,5-triazine.

20. A method of treating leukemia in a subject comprising administering a therapeutically effective amount of a compound of the formula

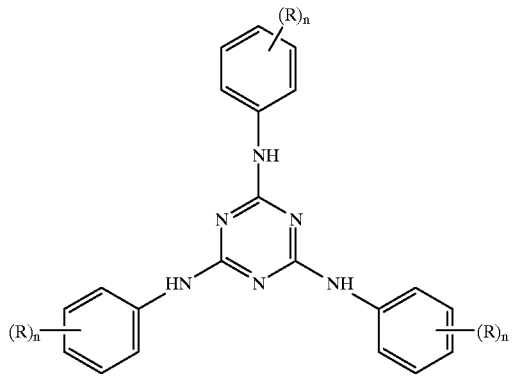

wherein each n is independently an integer of 1 to 5;

each R is independently halogen, hydroxy, mercapto, acyl, mercaptoalkyl, $(C_1-C_4)$ alkyl, $(C_1-C_4)$ alkoxy, $(C_1-C_4)$ alkylthio, $(C_1-C_4)$ hydroxyalkyl, $NR^1R^2$, nitro, cyano, $CF_3$, COOH, $SO_3H$, $SO_2NR^1R^2$ or $SO_2F$, where $R^1$ and $R^2$ are each independently hydrogen or $(C_1-C_4)$ alkyl; or a pharmaceutically acceptable acid addition salt thereof.

21. A method of treating breast cancer in a subject comprising administering a therapeutically effective amount of a compound of the formula

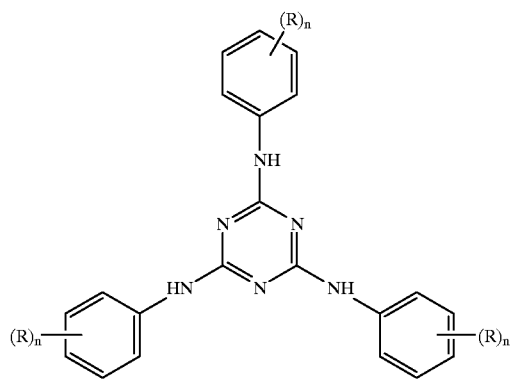

wherein each n is independently an integer of 1 to 5;

each R is independently halogen, hydroxy, mercapto, acyl, mercaptoalkyl, $(C_1-C_4)$ alkyl, $(C_1-C_4)$ alkoxy, $(C_1-C_4)$ alkylthio, $(C_1-C_4)$ hydroxyalkyl, $NR^1R^2$, nitro, cyano, $CF_3$, COOH, $SO_3H$, $SO_2NR^1R^2$ or $SO_2F$, where $R^1$ and $R^2$ are each independently hydrogen or $(C_1-C_4)$ alkyl; or a pharmaceutically acceptable acid addition salt thereof.

* * * * *

UNITED STATES PATENT AND TRADEMARK OFFICE
CERTIFICATE OF CORRECTION

PATENT NO. : 6,262,053 B1
DATED : July 17, 2001
INVENTOR(S) : Uckun et al.

It is certified that error appears in the above-identified patent and that said Letters Patent is hereby corrected as shown below:

<u>Title page,</u>
Item [75], Inventors, "Faith" should read -- Fatih --

Signed and Sealed this

Ninth Day of April, 2002

Attest:

JAMES E. ROGAN
*Attesting Officer*     *Director of the United States Patent and Trademark Office*